United States Patent [19]

Griffin

[11] Patent Number: 4,828,554

[45] Date of Patent: May 9, 1989

[54] ONE-WAY VALVE FOR LEG URINALS OR THE LIKE

[76] Inventor: Raymond E. Griffin, 22260 Davenrich St., Salinas, Calif. 93908

[21] Appl. No.: 125,169

[22] Filed: Nov. 25, 1987

[51] Int. Cl.⁴ ............................................... A61F 5/44
[52] U.S. Cl. ..................................... 604/350; 137/846; 383/44; 604/247; 604/283; 604/323; 604/326
[58] Field of Search ................... 604/30, 34, 128, 129, 604/246, 247, 255, 283, 323, 350, 322–331, 346–353; 251/336, 358; 137/511, 855, 856, 843, 846; 215/260, 311, 352, 354, 355, DIG. 3; 220/203, 308, 356–358; 383/42–44, 48, 49, 80

[56] References Cited

U.S. PATENT DOCUMENTS

| 564,502 | 7/1896 | Brookes | 137/846 |
|---|---|---|---|
| 984,808 | 2/1911 | Glocker | 215/352 |
| 1,022,141 | 4/1912 | Hurst et al. | 215/355 |
| 2,551,315 | 5/1951 | Christopher et al. | 383/44 |
| 2,572,383 | 10/1951 | Porter | 215/354 |
| 3,084,823 | 4/1963 | Reichstein | 215/311 |
| 3,118,468 | 1/1964 | Bochan | 137/846 |
| 3,463,159 | 8/1969 | Heimlich | 137/846 |
| 3,529,599 | 9/1970 | Folkman et al. | 604/323 |
| 3,886,937 | 6/1975 | Bobo et al. | 137/843 |
| 3,967,645 | 7/1976 | Gregory | 604/323 |

FOREIGN PATENT DOCUMENTS 2181951 5/1987 United Kingdom ............... 604/322

Primary Examiner—C. Fred Rosenbaum
Assistant Examiner—Mario Costantino
Attorney, Agent, or Firm—David D. Kaufman

[57] ABSTRACT

A one-way valve for a leg urinal or similar container comprising a thin, elastic tube formed with a permanent spiral twist giving it a memory that positively closes the tube against liquid backflow. The tube is nonetheless highly sensitive to internal pressure and unwinds to open the tube and permit forward liquid flow or even tiny volumes of liquid. The tube is stretch fit on an inexpensively molded nipple member and the tube and nipple member form a unit that is readily operationally insertable into and removable from the container to be discarded and replaced or to permit easy access for cleaning the container.

13 Claims, 1 Drawing Sheet

U.S. Patent
May 9, 1989
4,828,554
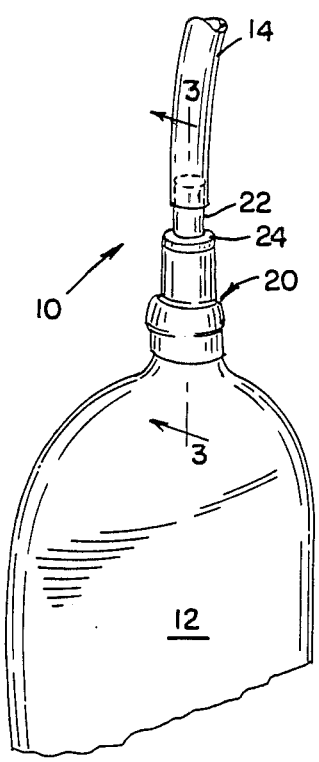
Fig. 1
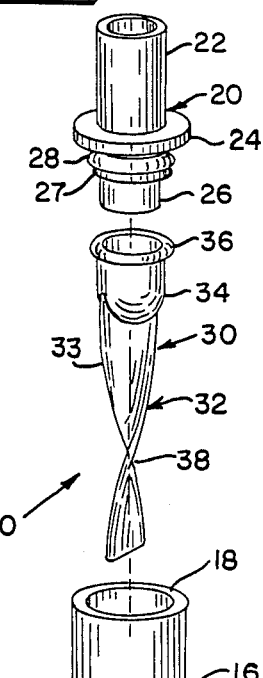
Fig. 2
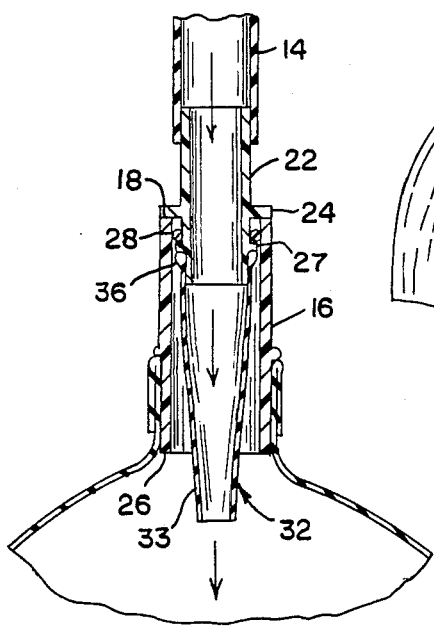
Fig. 3
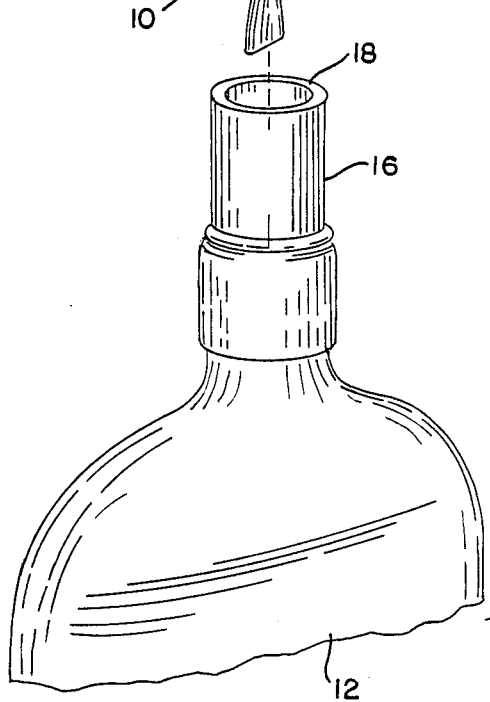

ONE-WAY VALVE FOR LEG URINALS OR THE LIKE

TECHNICAL FIELD

This invention relates to urine collection containers, such as leg urinal bags and the like, associated with user-worn catheters and, more particularly, to a one-way valve for such urinals permitting flow into the containers but preventing backflow therefrom.

BACKGROUND OF THE INVENTION

Many persons are compelled to be fitted with catheters, either permanently or temporarily, for the excretion or drainage of the contents of the bladder. Such persons include incontinents, quadriplegics, stroke victims and hospital patients. Catheters are of two basic types; internal, directly to the bladder so that relatively small quantities of urine are emptied more or less continuously, or external, whereby relatively large quantities of urine are excreted from time to time. In either case, flow of the liquid into the container must be unimpeded and backflow must be avoided.

The problems and dangers inherent in catheterized urine drainage and storage systems are well known. Thus, for example, blockage of forward flow can result in stagnation, bacterial growth and infection. Backflow of already excreted urine can have similar dangerous results in addition to unpleasant accidental staining of clothing or bedding. Where the system includes a collecton bag worn by the user, problems of hygiene and odor are always present unless disconnection and cleaning of the bag and attachments are readily achievable.

Numerous efforts have heretofore been made to provide a valve that efficiently and inexpensively overcomes the problems alluded to, but without complete success. Perhaps the most widely used catheter-urinal valve is the construction commonly known as a flutter valve, comprising a substantially flat tube of relatively thin, elastic material. The typical simple flutter valve has a normal slit opening and, depending on the gauge and elasticity of the material, requires substantial back pressure to close it. Thus, for example, a wearer of a leg urinal who lies down or raises his leg toward the horizontal could experience the flow of collected urine back up through the open slit of the flutter valve.

A highly specialized form of flutter valve is shown in U.S. Pat. No. 3,463,159 comprising a surgical instrument for chest cavity drainage of liquids, solids and semi-solids, such as blood clots, tissue, and the like. That valve is of appreciable length (3 inches) and width (1 inch) and is so constructed that substances pass slowly therethrough in a sort of peristaltic action, apparently initiated by the breathing and build up of air pressure in the chest cavity of the patient. For reasons that will be evident to those skilled in the art, the patented valve would not be suitable for leg urinal use.

A more sophisticated urine collection valve is shown in U.S. Pat. No. 3,967,645. In that structure a complex molded sealing member includes a pair of flat parallel leaves having an upper funnel-like shape, an annular top flange and relatively thick side flanges. Rigid clips or the like are clamped over the side flanges for the ostensible purpose of closing the normally open passage between the leaves. The sealing member is then operationally positioned in a rigid body member by screwing an upper body member to grip the top flange and a low friction washer is employed to prevent distortion of the sealing member during assembly. In addition to being complex, with a number of separate elements, that valve required somewhat difficult and cumbersome manipulations to operationally position or remove the same.

There thus exists a need for a one-way valve for catheter associated urine collection systems that is substantially trouble free and foolproof, simple to install and remove and of so little expense that the same may be discarded and replaced as desired.

SUMMARY OF THE INVENTION

The present invention provides a one-way valve for leg urinals and the like that is highly sensitive to permit forward flow of even drop-size volumes of liquid and yet is normally closed and insures against back flow under any conditions. The valve is of inexpensive and simple construction and assembly permitting easy connection to and removal from the container for cleaning purposes and/or discarding.

Briefly, the inventive valve comprises a thin elastic tube formed with a permanent spiral twist. The tube has a built in memory so that the same is always closed against any backflow. On the other hand, forward flow of any volume causes the spiral closure to untwist and open, permitting unimpeded forward flow. A rigid nipple member is operationally associated with the elastic spiral tube, the top portion of the nipple member being connectable to conventional tubing connected to the user's catheter. The nipple member is frictionally retained in a collar member forming a part of the liquid container and the spiral tube is stretch-fit on the lower portion of the nipple member that extends into the container. The assembled nipple member and spiral tube is readily removable from the container collar so that the entire assembly can be discarded and replaced. Removal of the assembly also permits ready access to the bag or other container with hose or faucet so that the relatively expensive and permanent bag may be rinsed and cleaned.

Numerous other advantages and features of the persent invention will become apparent from the following detailed description of the invention, from the claims and from the accompanying drawings.

BRIEF DESCRIPTION OF THE DRAWINGS

In the accompanying drawings forming a part of the specification, and in which like numerals are employed to designate like parts throughout, FIG. 1 is a perspective view illustrating operational assembly of the invention with a leg urinal bag;

FIG. 2 is an enlarged exploded view of the elements of the valve embodying the principles of the invention and illustrating the normally closed condition of the valve; and FIG. 3 is an enlarged sectional view on the plane of line 3—3 in FIG. 1 and illustrating the open condition of the valve.

DETAILED DESCRIPTION OF THE INVENTION

Referring in greater detail to the Figures of the drawings, the reference numeral 10 indicates generally a one-way valve embodying the principles of the invention. The valve 10 is shown operationally mounted in a leg urinal bag 12 which may be of conventional expansible form and material, such as vinyl. In use, the bag 12 is worn strapped around the leg of a user and is connected to the user's catheter by conventional latex tubing 14.

A collar member 16 is fixedly mounted in the top neck of the bag 12 by any suitable means such as heat welding, adhesives or clamp means. Typically, the collar member 16 is rigid and made of a hygienic, non-porous plastic such as polypropylene. As illustrated, the collar member 16 provides a relatively large diameter annular access opening 18 to the interior of the bag 12.

The valve 10 is operationally mountable in the collar member 16 and comprises an assembly including a nipple member 20 and a valve member 30. Nipple member 20 comprises a rigid cylindrical body having a top or upstream segment 22, a medial cap flange 24 and a bottom segment 26. An annular ridge 27 is formed on the bottom or downstream segment 26 and a compressible O-ring 28 is mounted and retained thereon beneath the cap flange 24. As indicated, the bottom segment 26 and ridge 27 are of smaller diameter and insertable into the collar member 16, while the cap flange 24 is dimensioned to fit on and nicely close the access opening 18. Preferrably, the nipple member 20 is integrally molded of a non-porous plastic like polypropylene. The O-ring 28 snugly but slidably retains the nipple member 20 in the collar member 16 and, for this purpose, is made of a suitable low-friction material such as neoprene.

The valve member 30 comprises a flexible and elastic tube 32 having a substantially flat segment 33 and a slightly bulbous upper segment 34 terminating in a reinforcing bead 36. The bulbous segment 34 and bead 36 are stretch-fit over the bottom segment 26 of the nipple member to operationally retain the valve member 30 thereon. It is important to note that the tube 32 is substantially flat and spiral-shaped, being formed with a permanent twist 38 intermediate its length so that the valve member is normally closed and thereby provides a positive seal against any liquid back flow. The valve member 30 preferably is made by dip-mold processes of thin gauge latex, on the order of 10 to 14 mils thick. In addition, the tube 32 is relatively narrow in width (approximately ⅜ inch) and short so that only aproximately ¼ inch extends beneath the collar member 16 into the bag 12. Thus, this very light gauge, flexible and elastic tube 32 is highly sensitive and reactive to any internal pressures from upstream. As a result, even a drop or two of liquid entering the tube 32 will cause the same to unwind the spiral twist 38 and permit unimpeded flow therethrough as illustrated in FIG. 3. Release of the internal liquid pressure results in the built-in memory automaticallly returning the tube to its normally closed spiral shape.

It should be noted that the entire valve assembly including the nipple member, O-ring and elastic tube is frictionally retained and easily positionable in and removable from the collar member 16 as a unit. Ready access to the bag through the collar opening 18 for cleaning purposes is thus a simple matter. Furthermore, since this entire valve assembly comprises a relatively inexpensive unit, the used units may be discarded and replaced on a frequent basis, perhaps even daily.

It will be appreciated from the foregoing detailed description of the invention and illustrative embodiment thereof that numerous variations and modification may be effected without departing from the true spirit and scope of the novel concept of the principles of the invention.

What is claimed is:

1. A leg urinal comprising:
    a flexible container suitable for wearing by a user thereof;
    a one-way valve having a nipple member, said nipple member having upstream and downstream ends with said upstream end operationally connectable to a user's catheter and said downstream end being removably connected in fluidwise communication to said container; and
    a thin, elastic tube attached to the nipple member, said tube comprising a substantially flat segment having a permanent spiral twist intermediate the ends thereof to positively seal the tube against liquid backflow but being responsive to liquid pressure to untwist, thereby opening the tube for gravity flow of liquid therethrough.

2. A leg urinal according to claim 1 wherein said nipple member comprises a rigid cylindrical body having an upstream segment connectable to the user's catheter and a downstream segment positionable in a top portion of the container, said tube having an upstream end stretch fit on said nipple member downstream segment.

3. A leg urinal according to claim 2 wherein the top portion of the container comprises an open top annular collar member, and retaining means on said nipple member for frictionally retaining said nipple member in said collar member.

4. A leg urinal according to claim 3 wherein said retaining means comprises an O-ring carried on the downstream segment of said nipple member and being snugly press-fittable in said collar member.

5. A leg urinal according to claim 4 comprising an integral flange on said nipple member which extends radially outwardly from the nipple member a sufficient distance to engage and close the open-top of said collar member when the nipple member is operationally positioned therein.

6. A leg urinal valve according to claim 5 comprising an integral ridge on the downstream segment of said nipple member, said O-ring being mounted on said downstream segment between said ridge and flange.

7. In combination with a leg urinal having an annular top collar, a one-way valve assembly comprising:
    an open-ended rigid cylindrical nipple member having an upstream segment, a downstream segment and an integral annular flange therebetween, said upstream segment having means for operational connection to the catheter of a user of the urinal said downstream segment being removeably connected to said annular top collar;
    sealing means mounted on said downstream segment; and
    a thin elastic tube stretch fit on said downstream segment, said tube having closure means positively closing said tube against liquid backflow but being responsive to internal liquid pressure to open and permit gravity flow of liquid therethrough.

8. The combination according to claim 7 wherein said closure means comprises a spiral twist permanently formed in said tube.

9. The combination according to claim 8 wherein said sealing means comprises · a compressible O-ring mounted on said nipple member downstream segment.

10. The combination according to claim 9 wherein said nipple member comprises an annular ridge integrally formed on said downstream segment spaced from said annular flange, said O-ring being mounted between said ridge and flange.

11. A one-way valve assembly for a leg urinal having a rigid annular top collar, said assembly comprising:

an open-ended rigid cylindrical nipple member having an upstream segment, a medial annular flange, a downstream segment and an annular ridge on said downstream segment spaced from said flange, said upstream segment being connectable to a catheter of the leg urinal's user and said downstream segment being operationally positionable in said collar;

a compressible O-ring mounted on said downstream segment between said ridge and flange; and a thin, substantially flat elastic tube stretch fit on said downstream segment, said tube having closure means positively closing said tube against liquid backflow but being responsive to internal gravimetric pressure as low as is created by drop size volumes of liquid to open and pass liquid therethrough, said assembly being operationally insertable as a unit in said collar whereby said O-ring frictionally engages the annular inner walls of said collar and said flange closes the open top of said collar.

12. A one-way valve assembly according to claim 11 wherein said closure means comprises a spiral twist permanently formed in said tube intermediate the ends thereof, said twist normally closing said tube but responding to internal liquid pressure to unwind and open said tube to pass liquid therethrough.

13. A one-way valve assembly according to claim 12 wherein said elastic tube comprises a bulbous upstream segment and an end reinforcing bead, said bead and bulbous segment being stretch fit on the downstream segment of said nipple member.

* * * * *